United States Patent [19]

Stein et al.

[11] 4,098,267
[45] Jul. 4, 1978

[54] SYSTEM FOR DISPLAY AND ANALYSIS OF PHYSIOLOGICAL SIGNALS SUCH AS ELECTROCARDIOGRAPHIC (ECG) SIGNALS

[75] Inventors: Israel M. Stein, Boston; Ronald T. Peterson, Newton Upper Falls, both of Mass.

[73] Assignee: Clinical Data, Inc., Boston, Mass.

[21] Appl. No.: 813,403

[22] Filed: Jul. 5, 1977

[51] Int. Cl.² ............................................. A61B 5/04
[52] U.S. Cl. ............................................. 128/2.06 G
[58] Field of Search ..................... 128/2.06 A, 2.06 B, 128/2.06 G, 2.06 R, 2.06 V

[56] References Cited

U.S. PATENT DOCUMENTS

| | | | |
|---|---|---|---|
| 3,221,334 | 11/1965 | Jones, Jr. | 128/2.06 G |
| 3,267,933 | 8/1966 | Mills et al. | 128/2.06 A |
| 3,434,151 | 3/1969 | Bader et al. | 128/2.06 R |
| 3,613,669 | 10/1971 | Corbin et al. | 128/2.06 R |
| 3,853,119 | 12/1974 | Peterson et al. | 128/2.06 R |
| 4,006,737 | 2/1977 | Cherry | 128/2.06 G |

OTHER PUBLICATIONS

Graystone, "IEEE Transactions on Bio-Medical Engineering," vol. BMS-17, No. 4, Oct. 1970, pp. 349-350.

*Primary Examiner*—William E. Kamm
*Attorney, Agent, or Firm*—Martin LuKacher

[57] ABSTRACT

A system is described for displaying several lines of electrocardiographic (ECG) signals on a cathode ray tube screen for observation, analysis and selection of those portions of the signals which indicate abnormalities of heart rhythm and cardiac events of interest to the diagnostician or trained observer. The ECG signals may be recorded at real time but are inputted to the system at much greater than real time. The system provides the display of the signal portions which were recorded consecutively, each on a separate vertically displayed line. In the system the greater than real time ECG signals are converted into consecutive bytes of data and transferred through a memory, which may be part of a computer, to a bulk storage unit such as a magnetic disc unit. The data from the disc is transferred to the display by way of the memory such that the display is continuously refreshed while the lines of ECG signals are under observation. Together with the ECG signals, other alphanumeric data, such as the time of day when the signals were recorded, patient name, heart rate, cardiac condition, and other pertinent information, may also be displayed simultaneously with the lines of ECG signals by the use of the memory and storage means to receive and hold such data. As consecutive sets of lines of the ECG signals are presented for display, sections of each line containing abnormalities and cardiac events of interest may be identified by an observer and transferred through the memory to the storage unit. Hard copy of the selected sections may be obtained as by a readout means such as a plotter which is responsive to data corresponding to the selected sections. The selected data may be applied to the readout means upon completion of the display of the entire long-term electrocardiographic recording and after operator review of the selected sections.

27 Claims, 15 Drawing Figures

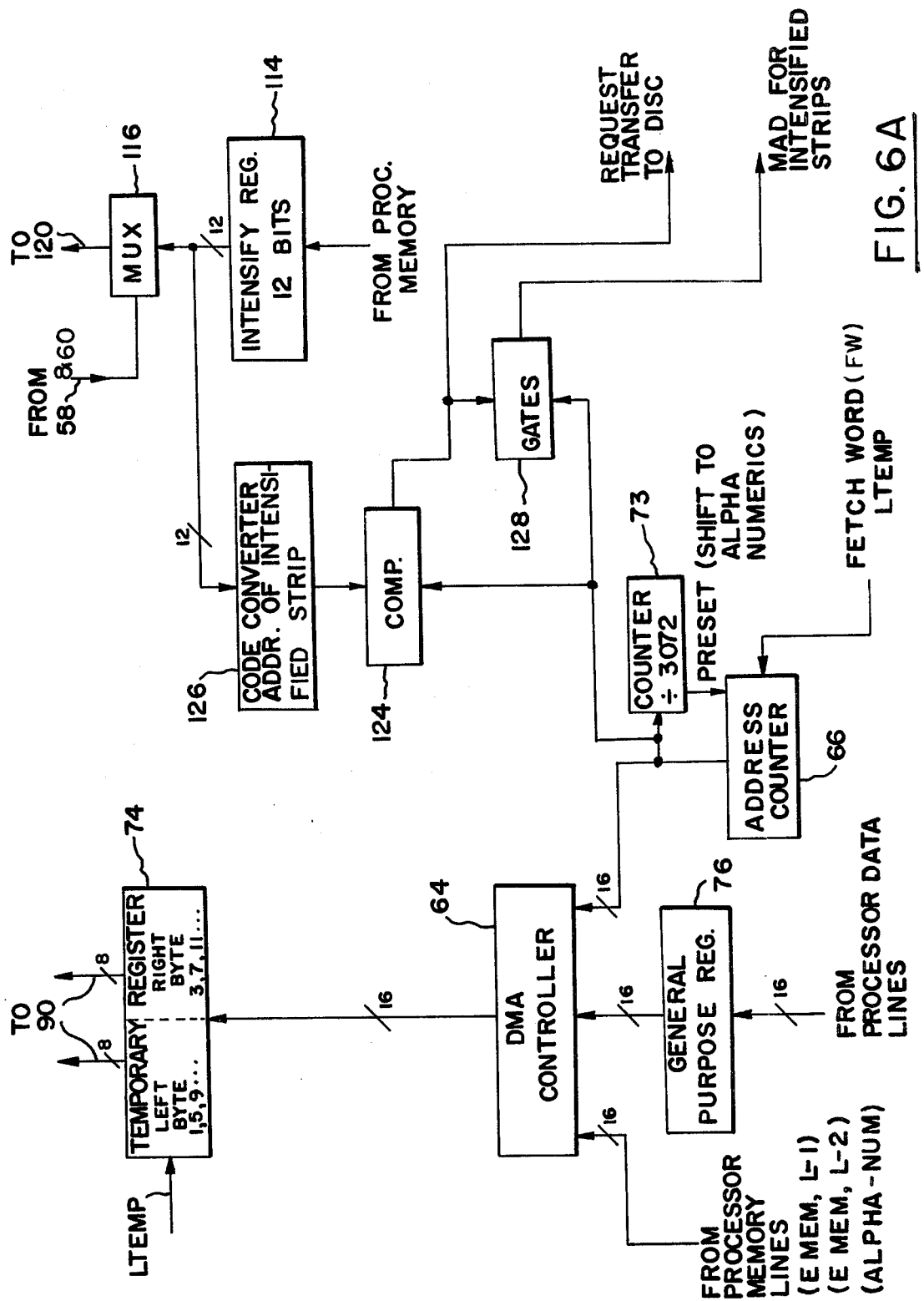

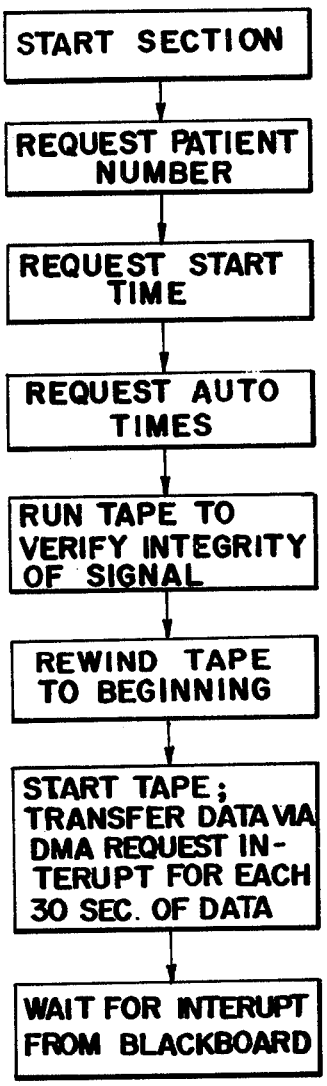
FIG. 10A
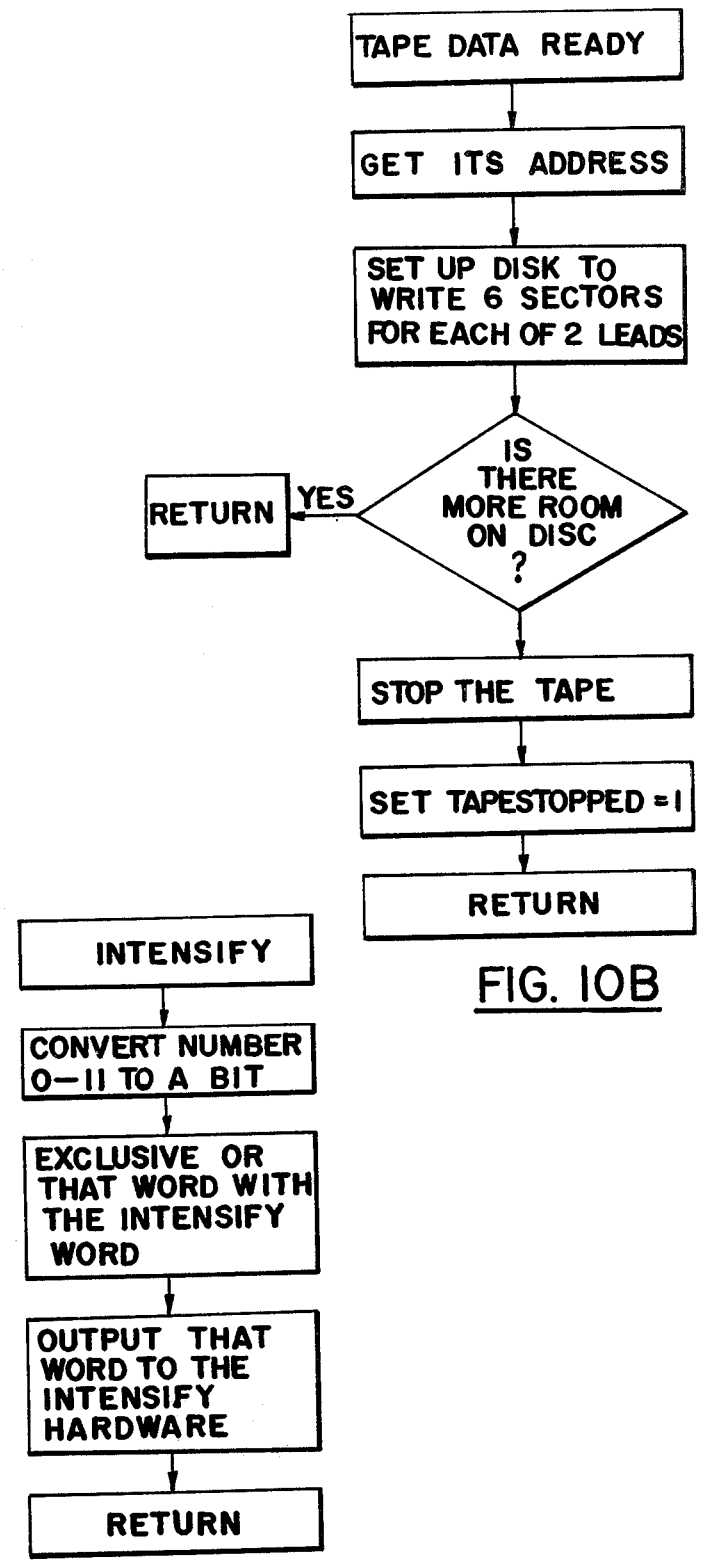
FIG. 10B
FIG. 10C

SYSTEM FOR DISPLAY AND ANALYSIS OF PHYSIOLOGICAL SIGNALS SUCH AS ELECTROCARDIOGRAPHIC (ECG) SIGNALS

The present invention relates to systems for display and analysis of physiological signals and particularly to systems for displaying electrocardiographic (ECG) signals such that sequences of said signals which represent abnormalities and other events of interest may be observed and selected for review, examination, and diagnosis by a physician.

The invention is especially suitable for use in processing long-term ECG signals which may be useful in the prognosis of heart disease as well as in the understanding of mechanisms of heart disease and in conducting studies and programs for patients who may have or who are likely to have cardiac diseases such as result in a myocardial infarction or sudden cardiac death. The invention is also suitable for display and analysis of other physiological signals such as electroencephalographic, electromyographic, impedance pneumographic, and blood pressure signals, especially where such signals are acquired over a long period of time.

The diagnosis and prevention of death and disability from heart disease often requires an analysis of an electrocardiogram obtained from a patient in the course of his normal activity over a long period of time, say of twelve or twenty-four hours duration. In order to make use of such long term electrocardiograms they must be reproduced at greater than real time rates, say sixty times real time, and those sections which indicate arrhythmias and other cardiac events of interest selected and presented for detailed observation by a physician.

The systems for display of long-term ECG signals at greater than real time rates have provided for the simultaneous observation of a pair of consecutive cycles or complexes of the signal. These complexes are usually superimposed upon each other as they flash upon an oscilloscope screen. The observer does not control the display but must make an observation very rapidly. Observers may be trained to detect and select cardiac abnormalities and events of interest through the use of such systems. These systems have serious disadvantages in that the display of an electrocardiographic sequence is sustained for only 5 to 20 milliseconds and the potential of missing significant data is high. Furthermore, the demands for intense concentration on the moving display results in high observer fatigue with further potential loss of significant data. Even with the addition of buffer storage means for the ECG signal data, the high speed at which the ECG signals are reproduced on these conventional displays can from time to time create fatigue for even a highly trained observer and result in observer error in following the display and selecting the desired sequences. In addition, the record, usually a magnetic tape on which the signals are recorded, must be stopped to allow time for the observer to examine sequences displayed at high speed. Each time this tape is started and stopped, errors in the reproduced signals result as the tape speed drops and until the tape again comes up to running speed. It is also desirable to present the display in a manner to enable the selection of the desired cardiac sequences more rapidly than is possible with available equipment. It is further desirable to present the display in a manner which will enable a trained observer to select the sequences of interest with a reduced possibility of missing any abnormal sequences.

Further information respecting available systems for the display of long term ECG signals may be obtained from our U.S. Pat. No. 3,853,119, issued Dec. 10, 1974, and from the patents referenced therein. Reference may also be had to the following patents in which various schemes for displaying ECG signals are described: U.S. Pat. Nos. 3,909,792 and 4,006,737.

Accordingly, it is an object of the present invention to provide an improved system for display and analysis of physiological signals.

It is a further object of the invention to provide an improved system for displaying physiological signals and particularly electrocardiographic signals in correct physiological order on a plurality of successive lines, each showing a portion of such signals as they occur notwithstanding that they may be reproduced for display and analysis at greater than real time.

It is a still further object of the present invention to provide an improved system for displaying ECG and other physiological signals which are acquired over a long period of time and with their playback at high speeds in a manner whereby the display of such signals is continuously under the control of the observer of the display.

It is a still further object of the invention to provide an improved system for displaying and analyzing ECG and other physiological signals such that an observer may select sections of said signals which are displayed rapidly and accurately.

It is a still further object of the invention to provide an improved system for the display and analysis of long term ECG data at greater than real time rates, as such data is reproduced from a recording without requiring the recording to be stopped, and thus allows the recording to run continuously during reproduction thereby reducing errors or omission of data due to signal distortion of the reproduced signal as when starting and stopping the recording.

It is a still further object of the invention to provide an improved system for displaying and analyzing ECG and other physiological signals which enables data representing such signals to be handled efficiently and without the need for such computer processing as would require a large amount of computer time.

It is a still further object of the invention to provide an improved system for display and analysis of ECG and other signals which enables the display of signals derived simultaneously from a plurality of sources, such for example as a plurality of ECG leads and enables the data obtained from such sources during like periods of time to be displayed sequentially (for example ECG signals from a modified $V_s$ lead, following ECG data from modified $V_1$ lead, or vice versa).

It is a still further object of the invention to provide an improved system for displaying and analyzing ECG and other physiological signals which enables selected sections of such signals to be reviewed in correct physiological sequence, after observation and discrimination of such sections from a long term recording of the signals, so as to provide an edited record of sequences reflecting abnormalities or events of interest for examination and diagnosis by a physician or other trained observer.

Briefly described, the invention involves the digitization of ECG or other physiological signals which may be derived as from a tape at greater than real time rates. A plurality of simultaneously recorded signals, as from different ECG leads, may be recorded on separate tracks on the tape. There may also be recorded timing signals which may be used to indicate the time of day as the ECG recording is made. These timing signals may also be used to control synchronous readout of the signals from the tape. The system may have separate means for handling the data for each signal channel. Since such means may be identical, only one will be described as this brief description proceeds. The system includes means for displaying, as on a cathode ray tube screen, on a plurality of separate lines, a plurality of successively occurring portions of the signals. Memory means are provided for containing data representing the signals as may be inputted to the memory means from buffer registers which organize the data such that alternate increments of the signals are displayed, thus utilizing only the resolution of the signals necessary to enable the discrimination of events of interest while efficiently utilizing data handling and memory capacity in the system. The system has selection means for identifying data in the memory means which represents sections of each of the lines while the lines are being displayed. Storage means are provided for receiving and holding the data identified by the selection means. The identified data is received in the storage means when the next plurality of successively occurring portions is displayed on the screen. The display is entirely under the control of the observer who makes the selection so as to enable the observer to rapidly and accurately discriminate and select the sections which exhibit abnormalities or other events of interest. Furthermore, the system is adapted for use under computer control for detecting heart rate and other significant cardiac events in order to examine the displayed data and with feedback respecting the displayed data to correct detection sequences, to refine the ability of the computer control system to recognize significant cardiac information related to the patient being examined, and to allow the observer to correct computer errors.

Readout means are provided for utilizing data held in the storage means to reproduce, as by plotting on hard copy, the signals in each of the identified sections of the line. The memory means may be the memory unit of a mini-computer, while the storage means may be a bulk storage unit such as a magnetic disc unit.

The invention itself as well as the foregoing and other objects, features and advantages thereof and a preferred embodiment thereof, will be more readily apparent from the following description when taken in connection with the accompanying drawings in which.

Figure 1:
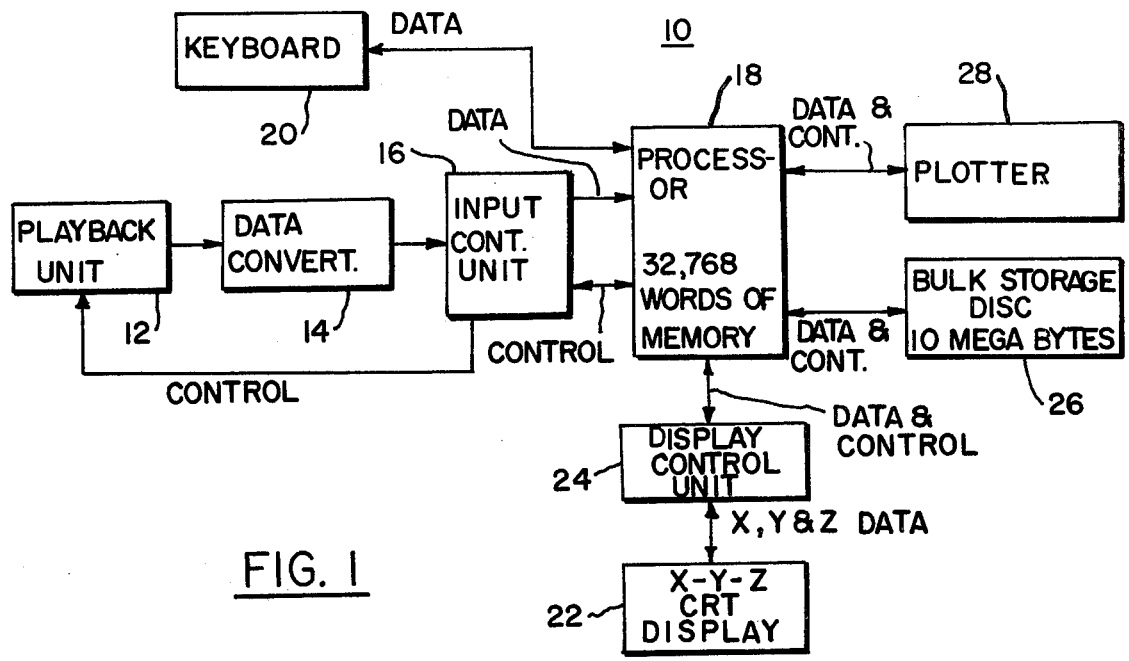
FIG. 1 is a block diagram showing a system for display and analysis of ECG and other physiological signals in accordance with the invention.
Figure 7:
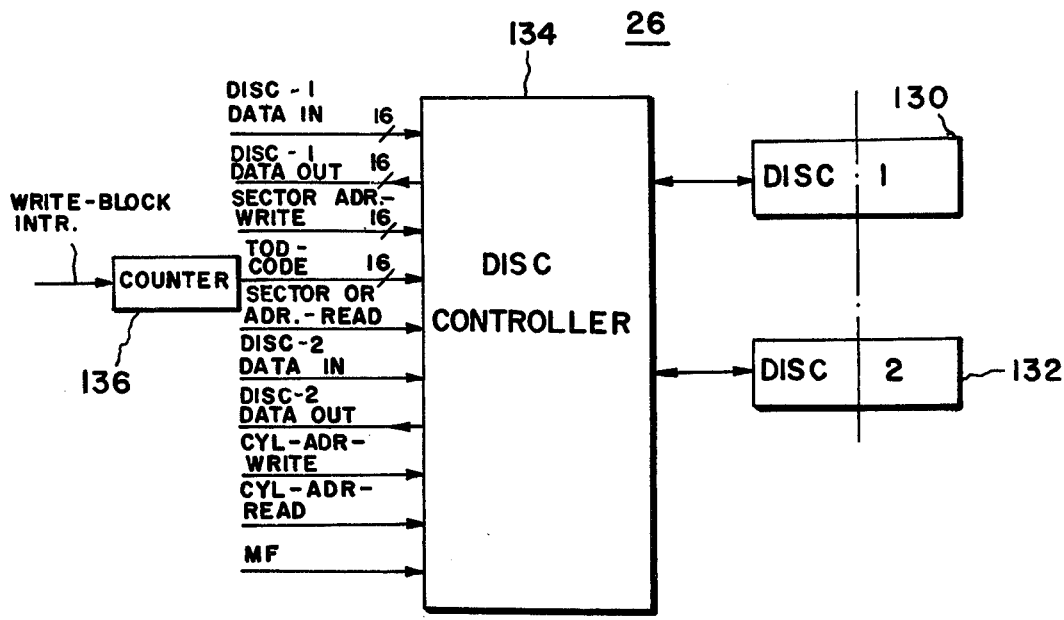
Figure 6:
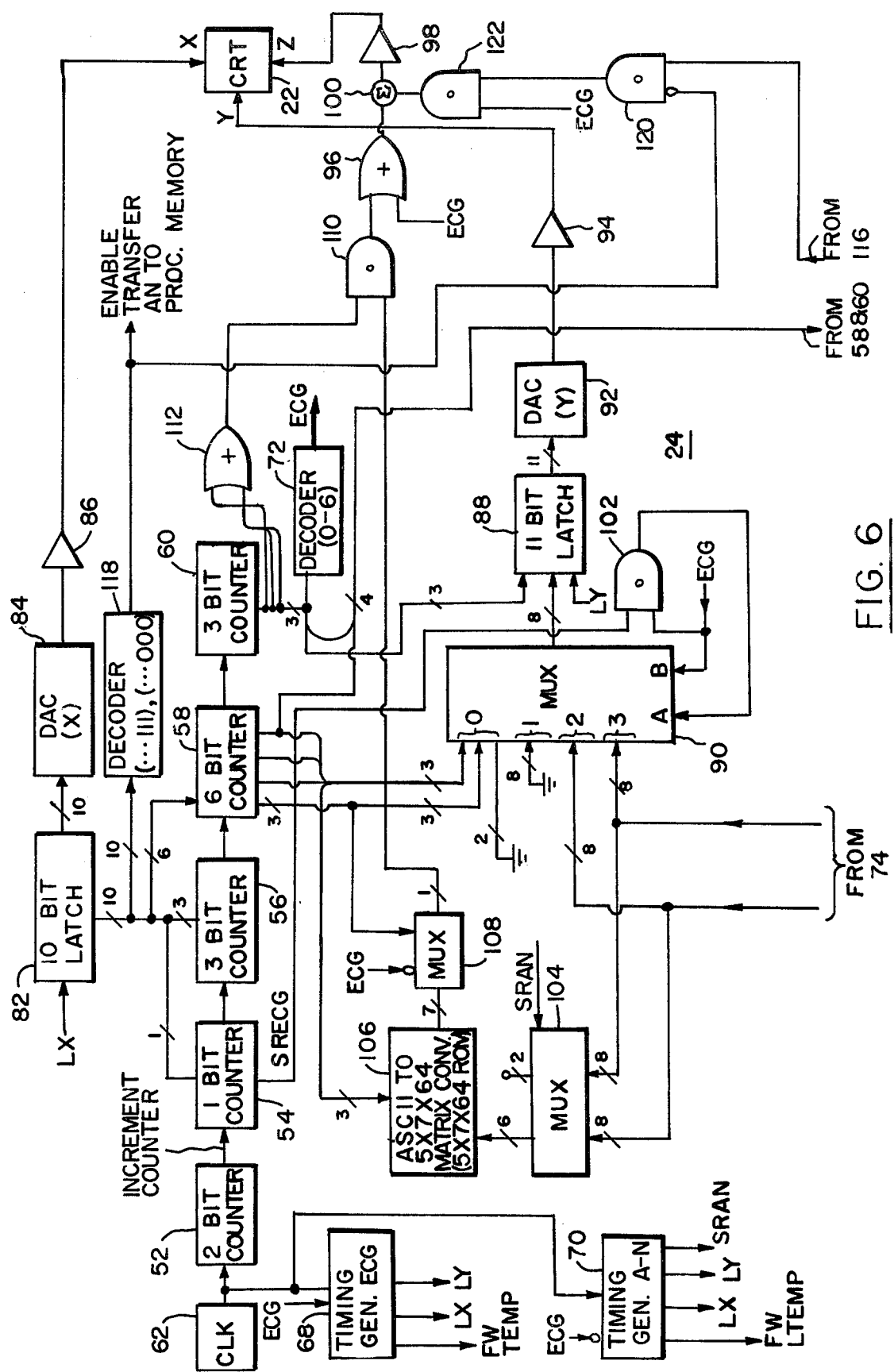
Figure 8:
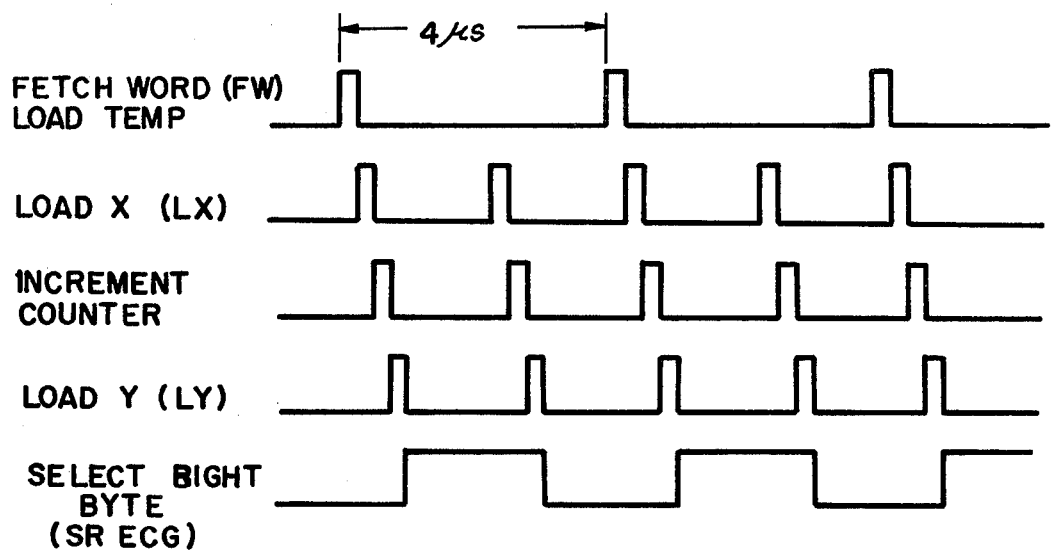
Figure 9:
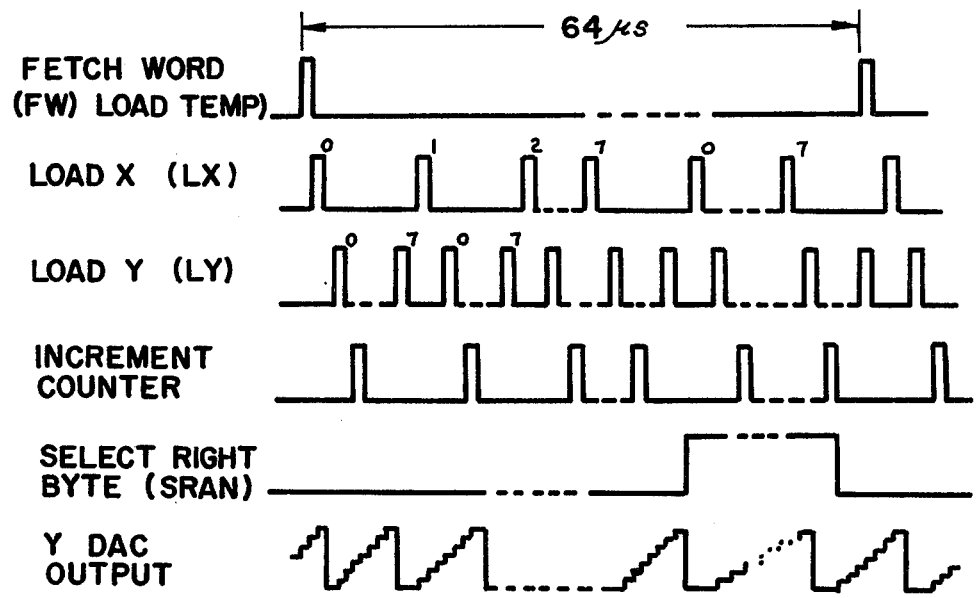

FIGS. 6 and 6A are a more detailed block diagram of the display control unit and of the equipment associated with the cathode ray tube (CRT) in the display of the system shown in FIG. 1; and FIG. 7 is a block diagram illustrating the bulk storage unit used in the system shown in FIG. 1; and FIG. 8 is a timing diagram showing the operation of the display and display control unit in producing traces of the ECG signals on the CRT screen;

FIG. 9 is a timing diagram illustrating the operation of the display and display control unit in forming the characters of alphanumeric data on the CRT screen; and FIGS. 10A through 10E are flow charts showing the operation of the system shown in FIGS. 1, 3, 6, 6A and 7.

Referring first to FIG. 1, the entire system for display and analysis of ECG signals 10 is shown. Tapes which may have 12 or 24 hour long-term recordings of the ECG signals to be analyzed and displayed are mounted in a play-back unit 12 and supply the ECG signals to a data converter 14 which translates these signals into digital form. When a timing signal is recorded on the magnetic tape with the ECG signals, the ECG signals are successively sampled under the control of the timing track signal and converted into 8-bit bytes of digital data. If a timing signal is not recorded on the tape a local oscillator is used to control the sampling rate. An input control unit 16 formats alternate bytes into consecutive words (see FIG. 4) and these words are outputted onto data lines to a processor 18. The input control unit, operating through a DMA channel as will be discussed in connection with FIG. 3, places the words in the memory of the processor 18. Only after an entire block is ready in memory will the processor 18 respond to an interrupt and then initiate a DMA transfer to a bulk storage unit 26 which may by the disc storage device. The processor 18 has a 32 kiloword memory (i.e., it has storage for 32,768 words in its memory).

Control for the system is provided by a keyboard 20 which is also connected to the processor data lines. The system functions to move the tape forward at play-back speed, to reverse the tape and to move the tape at fast forward speeds. These functions are all under keyboard control. The keyboard also controls the display of successive presentation of portions of the ECG signals as they appear in real time. A key on the keyboard selects successive 2-minute portions of the ECG and permits the operator to examine the ECG looking both forward and backward in time as may be required for accurate analysis. The keyboard is used to select portions of the display (viz, strips of the ECG which exhibit abnormalities of heart rhythm or cardiac events of interest) and to condition the system to store the ECG signals for these strips, together with the time of day when they were recorded, for review and printout onto hard copy after the entire tape has been analyzed. Other functions, such as the selection of alternate ECG channels, when two channels from different leads are recorded, are also controlled by the keyboard.

The processor 18 may suitably be a Nova 3/12 computer manufactured by Data General Corporation, Southboro, Massachusetts, 01772. Other mini-computers may also be suitable. The keyboard 20 may be a teletypwriter (TTY) keyboard which is connected to the computer data lines by way of an interface. The Model No. 4007 TTY Interface, available from Data General Corporation, may suitably be used. The input control unit 16 interfaces with the processor 18 by direct memory access (DMA) techniques. Control for the playback unit 12 may be directly from the processor 18 but is preferably via the control unit 16. The playback unit is controlled to stop automatically when the memory storage capacity of the disc 26 for ECG data is reached. Other playback unit controls, such as starting tape may also be automatic or set by the keyboard 20.

The processor 18 interfaces with an X-Y-Z cathode ray tube display 22 through a display control unit 24. The control unit provides for direct memory access to the processor memory of blocks of data for displaying two minutes of ECG recording continuously until the operator, by keyboard control, selects the next 2 minutes or returns to preceding 2 minutes. The sections of the display (strips) which are of interest (e.g., contain abnormalities) are marked as by being intensified. These sections are stored in the system for later review and printout. The CRT display 22 may suitably be a CRT monitor of the type used in graphic computer terminals. The CRT monitor manufactured by Hewlett Packard Corporation of Palo Alto, California, is suitable.

Also displayed are alphanumeric data to indicate to the operator the status of the system, for example that data is still available, is ready for display, etc., and the time of day at which the ECG portions being displayed were recorded. Also displayed may be a legend, referred to hereinafter as "auto time" which are particular times of day when certain cardiac events of interest were noted by the patient or his physician. For example, the time of day when certain stress conditions occur may be an auto time. The patient's number, the auto times and the time of day that the recording started (viz, when the patient was hooked up to the recorder by the physician) are all inputted to the processor from the keyboard 20.

The bulk storage unit 26, suitably a disc memory having the capacity of 10 megabytes (5 million 16-bit words) is connected to the processor and stores the blocks of data for display. Also stored on the disc 26 are the strips selected as the analysis of the tape proceeds together with the alphanumeric information, such as the time of day of recording of each strip selected, which is associated therewith. The disc 26 suitably has two disc elements or packs. There are 408 cylinders per disc surface. Four surfaces are available. Each cylinder has capacity for sixty seconds or one minute of ECG data. There are 12 sectors per cylinder, each of which sectors have capacity for five seconds of data. 5 seconds of data are converted by the data converter 14 into 512 bytes. Each sector thus contains a block of data. Four such blocks (a 20-second portion of the ECG recording) is displayed on each line of six lines of ECG data (see FIG. 2) so that 2 minutes of data is simultaneously displayed. This 2 minutes of data is transferred from the disc 26 to the memory of the processor 18 when a request for a new display is made via the keyboard 20.

The display control unit 24 provides direct memory access to the memory of the processor 18. The time of day and other alphanumeric information respecting each 2 minutes of data being displayed is stored in the processor memory for the period that each such 2 minutes is displayed. The lines of ECG data are consecutively transferred to the display 22 via the display control unit 24 such that the diplay is continually refreshed and remains visible, without flicker, on the screen. While the display is on the screen, sections of the lines which exhibit abnormalities or other events of interest may be selected and placed in designated areas of the disc 26 via the processor 18. The disc 26 may suitably be provided with capacity for 1000 of such intensified sections or strips. After the tape has been analyzed these sections may be transferred to the processor memory, accessed by the display control unit 24 to the display 22, and display for review. If the observer determines any such sections, upon review, not to be significant, he operates the keyboard 10. Each such section is then flagged and information as to the flags is stored in the processor 18. Preferably this flag information is not transferred to the disc but is used to determine which sections are to be ignored as upon transmission to a utilization device, such as a plotter 28 or a data link.

The plotter 28, which may suitably be an electrostatic plotter, receives the data for the selected strips. Only the data with respect to the strips that have not been flagged during review are transferred to the plotter. Also transferred is the information as to the time of day when the segment was recorded. The transfer to the plotter may be by way of the output half of the TTY interface to another computer designed to accept several such inputs or may be via a plotter to computer interface. Data is transferred one byte at a time. The electrostatic plotter may be controlled by a computer driver which receives the data and formats the data into successive lines. These lines of ECG signal are recorded as a sequence of dots by the electrostatic processor and hard copy of the ECG signals in 7½ inch strips across the width of an 8½ inch wide paper sheet in the form familiar to physicians is provided. The time of day may be printed along the edge of the sheet by the plotter. Such computer drivers and electrostatic plotters are commercially available. A suitable plotter and computer driver may be the Statos Model 4211 which is manufactured by VARIAN GRAPHICS of 611 Hansen Way, Palo Alto, California 94303.

Figure 2:
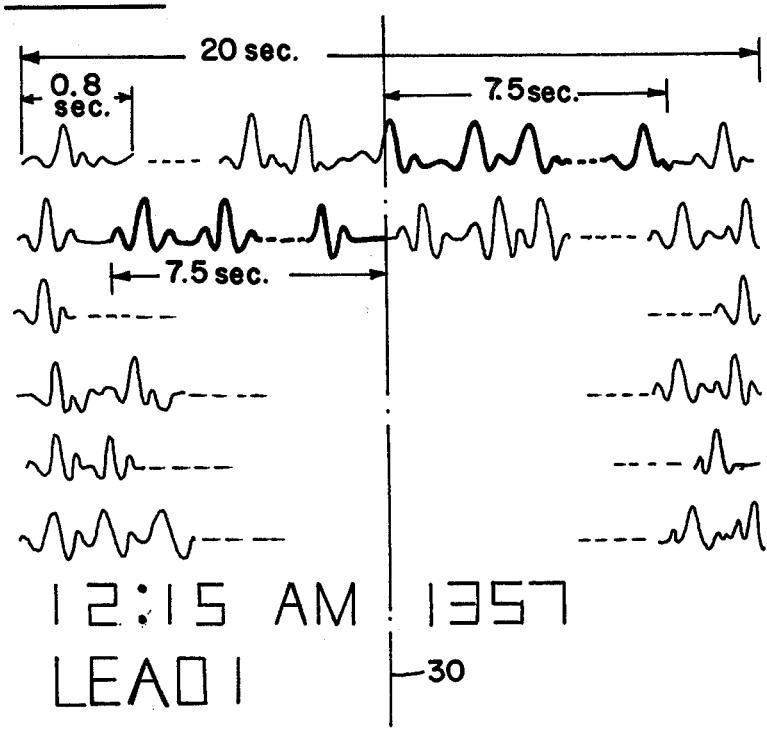
FIG. 2 is a diagram illustrating the display of ECG signals and other data on the screen of the display of the system shown in FIG. 1.

A typical 2-minute display is illustrated in FIG. 2. A center line 30 designates the center of the display. Each line is 20 seconds in duration. Ten seconds of the ECG data are displayed on each of the six lines on opposite sides of the center line 30 of the display. On the seventh and eighth lines of the display, alphanumeric data is displayed. This alphanumeric data may be the time of day of the recording of the first three lines and the code number assigned to the patient. However, this is optional. Underneath the time of day and on the eighth line there is displayed the lead or channel of ECG data. The bulk storage disc 26 has capacity for 12 hours of two-lead ECG data on each of the two disc units or packs (see FIG. 7). A separate lead or channel of ECG data is recorded on each of the two disc units or packs. A separate lead or channel of ECG data is recorded on each of the discs. The blocks of ECG data which are recorded on the tape at the same time are stored in corresponding locations on each of the disc units. By selecting the alternate lead, through the use of the keyboard 20, the same 2 minutes of ECG data but from the alternate lead, which have already been transferred from the disc 26 to a different part of the processor 18 memory will be accessed by the display control unit 24 and displayed on the CRT display 22. The disc itself is interfaced with the data lines of the processor 18 through a disc interface unit such as the Model No. 4234 disc interface manufactured by the Data General Corporation. The bulk storage disc 26 may suitably be the Model 44 disc memory manufactured by Diablo Systems, Inc., of Hayward, California.

The sections or strips on the display as shown in FIG. 2, which may be selected, are indicated as being 7.5 second segments or strips of each of the lines. Each complex of ECG data is approximately 0.8 seconds long. A 7.5 second strip provides a sufficient group of complexes and may be printed on a 7½ inche strip allotting 1 inch per second of ECG data. This scale is in accordance with standard ECG format which has been adopted over the years and is familiar to physicians and other workers in the art of electrocardiography. The bytes of ECG data corresponding to the 2.5 second regions at the ends of each line may be replaced with bytes of alphanumeric data such that a selected segment or strip contains the ECG data and the alphanumeric data representing the time of day of the recording. It is this information which is stored in the areas of the disc 26 allocated to the selected sections and is read out to the plotter 28.

The selected sections are intensified by an intensification control operated from the keyboard 20. In the event that ECG complexes of interest are not located towards the center of the display, the data for both leads may be moved in the processor memory by operating the keyboard. In other words the lines of ECG data may be shifted on the display, either to the right or to the left on each line. Then the intensified sections will contain the complexes which are selected. The selected sections are printed on the plotter and assembled into a report which can be delivered to the physician. The plotter 28 and its computer driver may be located remotely from the other parts of the display and analysis system, even in a remote city. Data links, either by telephone or other data communication techniques may be used to output the data through the processor 18 and its TTY interface or a high speed synchronous data modem to the remote plotter. Several plotters may be used, for example, a plotter and its associated driver at the same site as the rest of the display and analysis system and other plotters at remote locations which are interconnected by way of data links. In this manner several physicians may have the same data available to them immediately and consultation will be facilitated.

Figure 3:
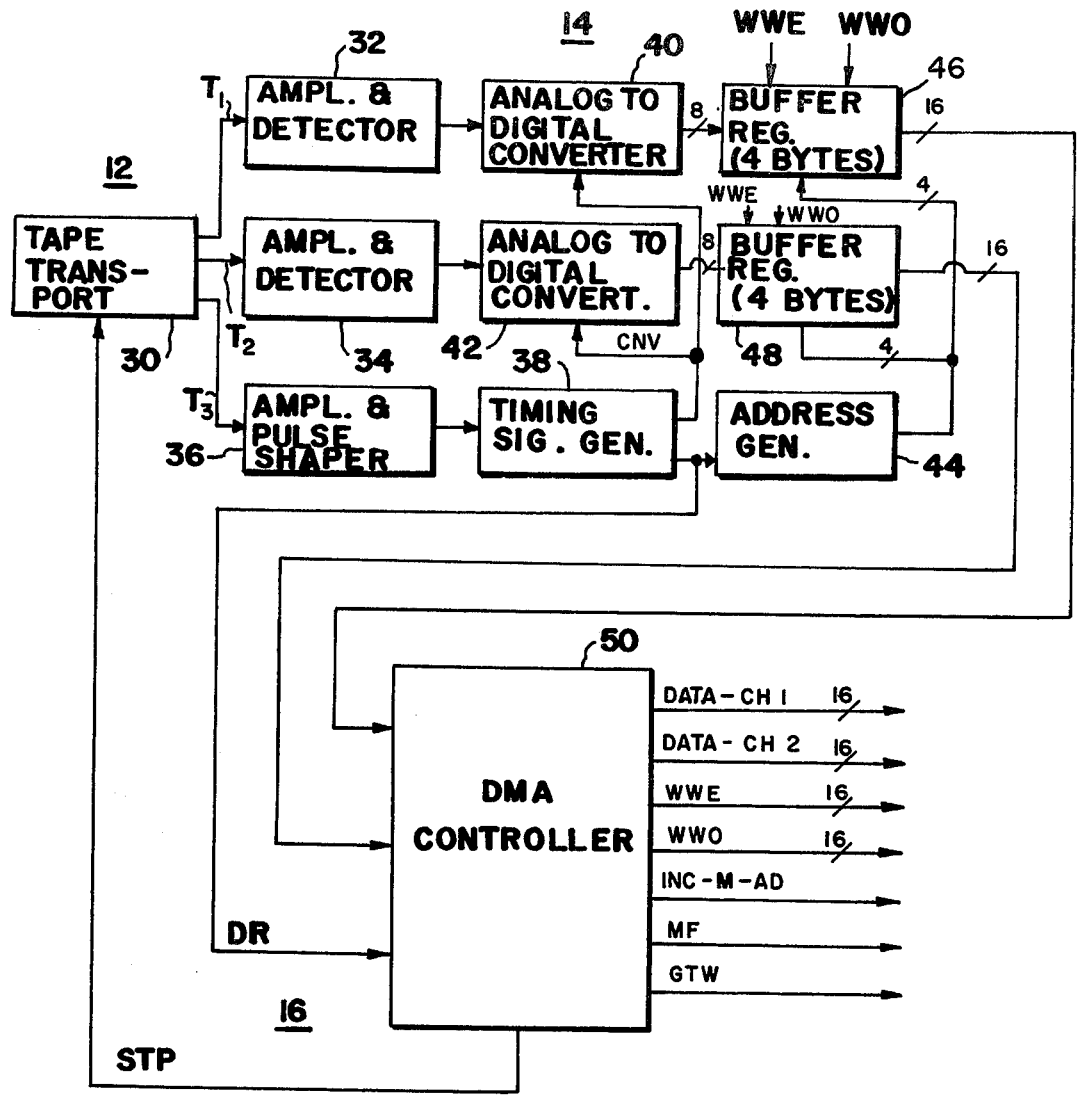
FIG. 3 is a more detailed block diagram of the playback data converter and input control units of the system shown in FIG. 1.

The elements of the system which are operative to input to the processor 18 the ECG data, are shown in greater detail in FIG. 3. The playback unit 12 is provided by a tape transport 30 having the mechanical drive system for transporting the tape across one or more magnetic heads which may scan three tracks on the tape. These are indicated as tracks $T_1$, $T_2$ and TT. On tracks $T_1$ and $T_2$ there may be recorded the ECG signals from lead 1 and lead 2 attached to the patient. Other types of physiological signals may also be recorded. A timing track TT is preferably recorded continuously as the ECG or other signals are recorded. The recording is made at extremely low speeds. The playback is however at much higher speeds, typically 60 times higher than the recording speed. Accordingly, the ECG signals appear upon playback at 60 times real time and 12 hours of recording will be reproduced in 12 minutes, and 24 hours in 24 minutes total time.

The ECG recording may be as FM analog signals and these signals, from each track, are detected and amplified in amplifier and detector circuits 32 and 34. The timing track may be a pulse recording and timing pulses are derived by amplifier and pulse shaper circuits 36. The pulses are used in the data converter 14 to drive a timing signal generator 38 which outputs convert command pulses (CNV) to analog to digital converters 40 and 42. When a timing signal is not recorded on the tape, the convert signal is synthesized by the playback circuitry. The timing signal generator 38 immediately thereafter but allowing time for the conversion in the analog to digital converters 40 and 42 to take place, outputs a data ready (DR) pulse to an address generator 44 which may be a 2-bit counter. If the analog to digital converters 40 and 42 generate a "done" signal when conversion is complete, these "done" signals are referably used to generate the data ready (DR) pulse. The address generator 44 outputs four bit addresses to buffer registers 46 and 48. One of the registers 46 is provided in the channel for lead 1 while the other register 48 is provided in the channel for lead 2.

Figure 4:
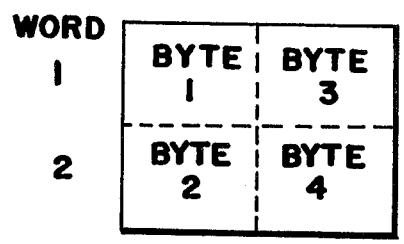
FIG. 4 is a diagram showing the organization of the data in the buffer registers of the system, which registers are illustrated in FIG. 3.

Each register 46 and 48 has storage for 4 bytes. These bytes, of 8 bits each, are inputted to the buffer registers 44 and 46 from the analog to digital converters 40 and 42. The addressing is such that alternate bytes are located in the same words as stored in the registers 46 and 48. The storage locations are shown in FIG. 4. In other words, even bytes and odd bytes are in consecutive words. Odd numbered words contain the odd numbered bytes and even numbered words contain the even numbered bytes. This organization or format facilitates the display for the reason that the resolution of the display is such that only alternate bytes, say those in the even numbered words, need be used to provide a high resolution display on which the operator can base his analysis of the ECG signals. The plotter 28 (FIG. 1) has higher resolution capability than the display and all of the words may be outputted to the plotter to enable the high resolution printout of the strips of ECG data. By way of specific example, the rate of conversion of the ECG signals as played back from the tape may be such that five seconds of real time data are converted into 512 bytes. The conversion goes on simultaneously for each of the two leads. Since the tape is played back at 60 times real time there will of course be 512 conversions in a 12th of a second. A display of the ECG data of high resolution on the CRT display 22 (FIG. 1) may be provided with half the number of bytes when such bytes are used alternately. The printout as on the plotter 28 utilizes each of the bytes so as to afford high resolution in the printout. The organization of the data into consecutive words of even and odd bytes facilitate the use of alternate bytes by relying on alternate words to produce the display. All of the words are however processed in the memory of the processor 18 and stored on the disc 26 so that the selected segments of ECG data are available for readout on the high resolution plotter 28.

Figure 5:
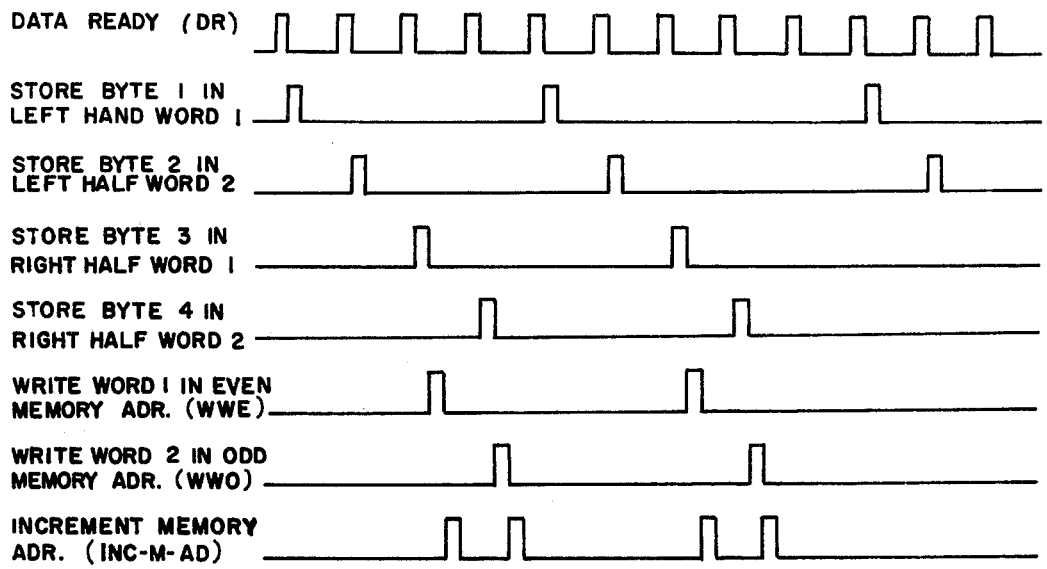
FIG. 5 is a timing diagram showing the timing of operations in the system shown in FIG. 3.

The manner in which the buffer registers 46 and 48 format the ECG data into words consisting of alternate bytes is illustrated further by the timing chart of FIG. 5. The data ready (DR) pulses increment the address generator 44 to produce successive commands on each of the four address lines to the buffer registers 46 and 48. The first DR pulse causes the generation of the store byte 1 command on the first address lines. The second DR pulse generates the store byte 2 command on the second address line, and so forth. Four consecutive DR pulses thus provide four different store byte addresses and the alternate bytes are entered as consecutive words in the buffer registers 46 and 48. The registers present 16 bit (two byte) words to a direct memory access (DMA) controller 50.

The buffer registers 46 and 48, the address generator 44 and the DMA controller 50 are all part of the input control unit 16. The DMA controller 50 provides direct access to memory locations in the memory of the processor 18 and serves as an interface to the processor 18. The controller has 16 bit data output lines for the ECG data for lead 1 (Data-CH1) and for lead 2 (Data-CH2). These words are stored in different memory addresses for even and odd words in the memory of the processor 18. The memory addresses are generated by a memory address counter which is located in the controller 50. Since the two different words from the two different leads may be stored in widely different memory locations, the controller may also change a high order bit along with the incrementing of the address counter when supplying the address for the DMA transfer so as to use a single address counter for DMA transfer of both words. The memory of the processor may have sections dedicated as buffers for incoming ECG data. Each of these buffers may have capacity for 30 seconds of ECG data (1536 words) or six blocks of 256 words (512 bytes) each. Two of these buffers are provided for each channel or lead.

As the bytes of ECG data are inputted to the buffer registers the DR signals are counted in the DMA controller 50 and a request is generated by the controller 50 to the processor to transfer the 30 seconds of ECG data to the disc 26. Each five seconds of data is then recorded in a different disc sector and six sectors are recorded on each transfer to disc. The transfer request is an interrupt shown as an output GTW from the DMA controller 50. When this interrupt is generated it enables another DMA request to transfer the data now in memory, to the disc 26 to be generated.

As shown in FIG. 5 for every pair of DR pulses, separate write word even (WWE) and write word odd (WWO) control signals are generated by the DMA controller 50 and inputted to the buffers 46 and 48 and to the processor 18. These may be pulses which condition the buffers to output the words consecutively and the processor to write these consecutive words alternately in even memory address locations and odd memory address locations in the buffer sections of the processor 18. Thus, by having access to even memory address locations for the bytes to constitute the display, the display will be provided from alternate bytes. The memory address counter is incremented by an output on the INC-M-AD line from the controller 50 which occurs immediately after the write word requests are outputted to the processor, as is shown in FIG. 5. When one of the 30-second buffer sections is filled the next 30-second buffer section will receive the data through the DMA controller 50. Data from the first section is transferred to the disc 26 before the second 30-second section is filled. Accordingly, the disc will continuously receive data and data may be transferred from disc to the memory of the processor under keyboard control for the display of successive 2 minutes of ECG data while the data is transferred from the tape through the memory of the processor 18 to the disc 26.

The disc has storage for 12 hours of two-lead ECG data. However, in order to minimize the number of times that the tape may stop during the analysis, it has been found preferable to cause the tape to stop when the disc has eleven hours of ECG data stored thereon. Accordingly, when the sector in the disc allocated to the last 5 seconds of the 11th hour is full, the disc outputs a memory full (MF) request to the processor (see FIG. 7). This request is transferred via the DMA controller 50 to the transport to stop the tape. The memory full request is not generated if the operator has displayed earlier periods of the ECG data. Thus, if in the eleven minutes preceding, the operator had scanned several of the first hours of the ECG recording the memory full (MF) request will be inhibited, such that the MF address is generated only when the operator gets behind in the analysis of the ECG data by 11 hours of ECG data. In most cases therefore the tape is stopped only once, if at all, during the entire analysis. The other transport command for fast forward and rewind may also be interfaced to the tape transport from the processor 18 by conventional tape transport interface techniques.

The DMA controller certainly is designed in accordance with techniques known in the art and may be of a design similar to DMA controllers supplied by the Data General Corporation, their Model No. 4042. See Data General Interface Designers Manual #015-000031-02.

The display control unit 24 is illustrated in FIGS. 6 and 6A. The CRT 22 has an "X" input which sweeps the beam horizontally from left to right so as to write the lines of ECG data and alphanumerics from left to right across the screen (see FIG. 2). The line which is written is selected by vertical deflection signals applied to the "Y" input of the CRT. The lines and characters are illuminated and intensified by signals applied to the "Z" input of the CRT 22. Both horizontal and vertical deflections for the X and Y inputs are generated by serially connected counters 52, 54, 56, 58 and 60. These counters are driven by a clock oscillator 62. Each line of ECG data corresponds to 20 seconds of recording. Each 20 seconds of recording is converted into 1,024 words. Using alternate ones of these words provides 1,024 bytes. There are therefore 1,024 bytes per 20 second ECG line.

To generate the requisite 1,024 step sweep in the horizontal or X direction, 10 bits are used. These 10 bits are provided by a 1-bit counter 54, a 3-bit counter 56 and a 6-bit counter 58 of the serial counters which are driven by the clock 62. In order to provide a flicker-free display it is desirable to scan the entire display at at least a 50 Hz rate. To this end the clock 62 may run at 2 MHz. This enables the words of ECG data to be fetched every 4 microseconds (see FIG. 8). The 1-bit counter 54 of the counters 54, 56 and 58 which count up to 10 bits is then incremented every 2 microseconds. The 3-bit counter 60 determines which of the eight lines of the display are scanned. Each time the 10-bit counter counts up to 1,024, the end of a line is reached and the 3-bit counter is incremented. The 3-bit words from the 3-bit counter 60 thus designate the line being scanned.

The seventh and eighth lines for alphanumeric characters are adapted to display 128 characters per line. Each character is generated in a sequence of eight steps in the horizontal direction. Only five of such steps are used to allow for spacing between characters. Accordingly, 128 times 8 or 1,024 steps in the horizontal direction provide for 128 characters per line. The height of the line displayed in the vertical or Y direction both for ECG data and alphanumerics is determined by the data. The blocks of data for the two minute display, a total of 6,144 words, is transferred from the disc 26 (FIG. 1) to the memory of the processor 18. A different 6,144 word group of blocks is transferred to the processor for each two-minute display when that display is called up by the keyboard 20. The alphanumerics associated with the display may be generated in the processor. For example, each disc sector corresponds to a different time of day. The time of day represented by the sector and the start time of the tape provide information as to the time of day when the ECG data which is displayed was recorded. The lead (either lead 1 or lead 2) is selected by the keyboard and may be converted into alphanumeric data for the display. The patient number is similarly inputted by the keyboard and may be translated into alphanumeric words for the display. These words are loaded into an alphanumeric section of the memory of the processor 18.

A DMA controller 64 provides direct access to the ECG data words from the even memory locations of the block and for the alphanumeric words, which ECG data words and alphanumeric words are in the memory of the processor 18. An address counter 66, which is incremented by the fetch word request generated by timing generators 68 and 70, provides access to the ECG words from the even memory location (EMEM) and to the alphanumeric words. The timing generator 68 provides the timing when the ECG lines are being displayed and the other timing generator 70 is used during the display of the alphanumeric (A-N) lines. In order to enable the ECG timing generator 68 during the scanning of the sixth ECG lines, a decoder 72 is connected to the 3-bit counter 60. When the counter 60 is in its first seven states (0 to 6) the ECG lines are being scanned. When the decoder is in states 7 and 8 the alphanumeric lines are scanned. The output from the decoder labeled "ECG" when asserted enables the ECG timing generator 68 and inhibits the A-N timing generator 70.

The first 3,072 fetches (FW) generate addresses for the 3,072 of the 6144 words which have even memory address, which even memory address words are used for the display of the ECG lines. A counter 73 which may count the fetch word commands or the 16th bit of the address counter output, presets the address counter 66 and shifts the addresses to select the alphanumeric word locations. Each line of 128 possible alphanumeric characters is then accessed by the controller 64 and supplied to a temporary register 74. In the case of ECG data the register will successively store the left and right bytes (1 and 3) of the first word, the left and right bytes 5 and 7 of the third word, the left and right bytes 9 and 11 of the fifth word, and so forth. It is the first, third, fifth, seventh ... words which are stored in the even memory address location in this exemplary system as was explained in connection with FIGS. 4 and 5. The function of the counters 66 and 72 may be obtained in the processor 18. For example, the addresses for ECG data lead 1 may be $4,000_8$ to $17,777_8$ and for lead 2, $44,000_8$ to $57,777_8$ (words). The lead 1 and lead 2 alphanumeric addresses are words $60,000_8$ to $60,077_8$ and $60,100_8$ to $60,177_8$ respectively. By using the counters 58 and 56 for the low order bits and forcing the high order bits to the appropriate levels, the data is fetched from the correct location in the processor memory.

A general purpose register 76 has data inputted thereto, from the processor 18 data lines, as to various control functions of the system (e.g., tape, transport control functions such as tape run forward, fast forward, rewind and stop). The general purpose register word also provides for selection of lead 1 or lead 2 blocks in the processor memory. The processor memory will have transferred thereto, when each two seconds display is requested, two groups of blocks of data each having 6,144 words. One of these blocks will be ECG data for lead 1 and the other for lead 2. The general purpose register sets the DMA controller 64 to access either one or the other of these blocks depending upon which lead is selected. Thus, display of the same 2 minute section from either lead may be obtained alternately by pressing an appropriate key on the keyboard 20 (FIG. 1). The general purpose register will also inhibit transfer of data from the ECG data locations (EMEM, L-1, or EMEM, L-2) so as to blank the ECG display. The alphaumeric display may similarly be blanked or the entire display blanked by means of the general purpose register when the keyboard keys for such blanking operations are depressed.

The lines of ECG data may be shifted either towards the left or towards the right by moving the data in memory as commanded by the keyboard.

During the display of the ECG data the timing generator 68 produces the command pulses, fetch word (FW) and load temporary register 74 (LTEMP). The fetch word command (FW) increments the address counter 66. The LTEMP command loads the word from the previous fetch into the temporary register 74. The timing generator 68 also provides load X command pulses (LX) which load the 10-bit word from the counters 54, 56 and 58 into a 10-bit latch 82. A digital to analog converter (DAC) 84 translates the 10-bit word into an analog signal which may be amplified in an amplifier 86 and applied to the horizontal or X input of the CRT 22 so as to scan the lines of ECG data from left to right (see FIG. 2). After each load X (LX) pulse from the timing generator, the display will be incremented by one of the 1,024 steps which constitute a horizontal line on the display.

The timing generator 68 also outputs a load Y (LY) pulse to an 11-bit latch 88. This eleven-bit latch receives data from a multiplexor 90 and from the 3-bit counter 60. The multiplexor 90 has four 8-bit input ports (1-4), an 8-bit output port, and control inputs A and B. The 3 bits from the counter 60 determine which of the eight lines of the display is being scanned. The multiplexor 90 is operated to select either the left or right byte from the temporary register 74 which are applied thereto at input ports 2 and 3 thereof. The 8 bits of the selected byte of ECG data determine the vertical displacement or height of the displayed ECG signal at each of the 1,024 steps in the horizontal or X direction. The load Y (LY) command stores the 11-bit word corresponding to the exact vertical displacement upon occurrence of the LY command pulse. A digital to analog converter 92 provides an analog signal, which may be amplified in an amplifier 94, to the Y input of the CRT 22. The X and Y commands thus place the beam of the CRT at an exact point on the ECG signal. The screen is intensified by applying a voltage to the Z input. Intensification is provided by the ECG output from the decoder 72. This output is applied to Z input of the CRT by way of an OR gate 96 and an amplifier 98 via a summing junction 100. The summing junction 100 also receives signals for intensifying the sections of the ECG display which are to be selected for subsequent review and readout. These intensify signals are also applied through the summing circuit 100 to the Z input of the CRT 22 and raise the level of illumination of these sections to distinguish them.

The switching of the input ports of the multiplexer 90 to the eight bit output thereof is controlled by logic levels applied to the control inputs A and B. When the ECG lines are displayed, the B input is asserted by the ECG output of the decoder 72. The A input is asserted on alternate steps of the 1,024 steps of the horizontal displacement in the X direction across the CRT 22. This alternate assertion comes about from the select right ECG (SRECG) output of the 1-bit counter 54 which is applied to the A input via an AND gate 102. The SRECG levels alternate each time the counter 54 is incremented. When the B port is asserted, the left byte section of the temporary register 74 is multiplexed to the output lines of the multiplexor 90. Similarly when the SRECG level is high the third port is multiplexed to the output of the multiplexor 90 and the right byte which is stored in the register 74 is outputted by the multiplexor 90. Accordingly, for each horizontal step across the ECG lines of the display an alternate byte of a successive even memory word is transferred to the latch 88 and converted into an analog signal which controls the vertical height of the display for that horizontal step. The ECG signals are therefore written as successive 20 second lines as illustrated in FIG. 2.

When the seventh line is reached, the ECG output of the decoder 72 is no longer asserted and the AND gate 102 is inhibited. The control levels on the control ports A and B of the multiplexor 90 are in a "00" state and the "0" input port of the multiplexor 90 is connected to the output port thereof. The display is then conditioned for alphanumerics.

Each alphanumeric character is scanned individually during eight load X (LX) pulses from the AN timing generator 70 which is enabled when the ECG output of the decoder 72 is absent, as shown by the inhibit symbol from the ECG line to an input of the timing generator 70. Seven load Y pulses (LY) are provided for each LX pulse. The timing generator 70 may include a rate multiplier which multiplies the clock pulses for this purpose. The 6 bits from the 6-bit counter 58 are applied to the "0" input port of the multiplexer 90 and loaded in the 11-bit latch 88 on each of the LY pulses. The output of the YDAC 92 is then a staircase as shown in FIG. 9. The staircase contains seven steps.

The data in the temporary register 74, when alphanumerics are fetched by the DMA controller 64, is translated into a single output for intensifying the beam of the CRT 22 when it reaches each of the steps in accordance with the alphanumeric characters represented by the bytes stored in the register 74. This is accomplished by means of a multiplexor 104 which selects either the left or the right byte in accordance with a select right alphanumeric (SRAN) level from the AN timing generator 70. Thus the left and the right bytes are alternately outputted by the multiplexor 104.

The ASCII code may be used to represent the alphanumeric characters. This code is a 6-bit code. Thus only six output bits are required from the multiplexor. This code is converted into a matrix of five columns and seven rows by a ROM which is a 5 × 7 × 64 matrix converter. Each ASCII byte conditions the converter to output the corresponding one of the 64 characters which it represents. One column of 7 bits is outputted at a time for each increment of deflection of the beam in the CRT 22 in the X or horizontal direction. The convertor 106 is conditioned to output one bit at a time for each increment in the X direction by the last 3 bits in the 6-bit counter 58. A successive one of these 7 bits is outputted upon occurrence of successive ones of the seven steps of the staircase by a multiplexor 108. This multiplexor 108, like the timing generator 70, is enabled in the absence of the ECG output from the decoder 72 (i.e., only during the writing of alphanumerics). The first 3 bits from the 6-bit counter 58 select the sucessive ones of the seven bits. These bits are applied through an AND gate 110 which is enabled when either of the last 2 bits of the 3-bits counter 60 is high via an OR gate 112.

The output of the AND gate passes through the OR gate 96 and the summing junction 100. It is amplified in the amplifier 98 and applied to the Z input of the CRT display 22 so as to intensify that display when the output bit from the converter 106 is present. If for example the alphanumeric character is a "1", all 7 bits will be present during the first staircase scan and a single line is written on the display. For more complex alphanumerics, different combinations of the 7 bits will be written on each of five successive scans (5 staircases). No bits are written on the sixth and seventh staircases so as to space the characters.

As shown in FIG. 2 selected sections of the ECG lines of 7.5 seconds duration which may be located in opposite sides of the center line of the display may be selected and stored in the disc 26 (FIG. 1) for later review and printout on the plotter 28. There are twelve possible selections on the six ECG lines. The selected strip (one of the twelve) is identified as a 12-bit digital number which is stored in an intensify register 114. This 12-bit number is generated in the keyboard and transferred to the register 114 via the memory of the processor 18. In the event the operator changes his mind he may cancel the selected strip (deintensify it) by making the same selection again. This will cause the 12-bit intensify number in the processor memory to be exclusive ORed and to output the results of the exclusive ORing operation again to the intensify register 114. The one of the 12 bits which was then asserted will then not be asserted and its corresponding segment of the display will become deintensified.

The bits in the intensify register 114 are outputted when their corresponding strip is displayed through the use of a multiplexor 116 which is controlled by the highest four bits in the string of counters 52 to 60. 3 bits from the counter 60 and the highest bit of the 6 bit counter 58 are applied to the multiplexor 116 for this purpose. In order to prevent intensification of the 2½ second portions of the opposite ends of each line, the 10 bits which determine the deflection in the horizontal or X direction are decoded in a decorder 118 which provides outputs when the 10-bit number consists either of "000" or "111" in its last 3 bits. An AND gate 120 is then inhibited from passing the intensified bit from the multiplexor 116 to another AND gate 122 which is enabled while the ECG lines are scanned by the ECG operator of the decoder 72. The level at the output of the AND gate 122 sums with the output of the OR gate 96 in the summer 100. A higher amplitude drive signal for the Z input drive amplifier 98 is then applied than is the case when an EGG line section is not selected and the selected strip is intensified.

In order to store the data for the intensified strips and the alphanumerics which are displayed concurrently therewith, the addresses from the address counter are compared in a comparator 124 with the addresses for the intensified strip. These addresses may be generated by a code converter 126 which converts the 12-bit intensify word in the register 114 into words which cover all address bits for the intesified strip. The comparator 124 then requests a transfer to disc of the words in the processor memory at the memory addresses for the intensified strips. These memory addresses are transferred to the processor 18 by way of gates 128. When the operator requests the next two minutes display the ECG data for the selected strips is transferred to a designated or dedicated disc areas which may have storage for 1,000 selected strips. The functions of the comparator 124, the converter 126 and the gates 128 may be implemented in the processor 18 and selected data may be transferred to the disc under program control.

The disc 26 is schematically shown in FIG. 7. There are two discs, disc 1, 130 for lead 1, and disc 2, 132 for lead 2. All of the information from lead 1 (track T1 of the tape, see FIG. 3) is stored in disc 1, 130, while the other disc 132 stores all the data from the second track T2. The data is transferred to disc through a disc controller 134 which is part of the disc unit 26. There are 16 bit data input and data output lines to the controller 134 from the processor 18. The processor also provides commands for the sector to be written in the form of a sector address ADR. Each time a request to write a block occurs a counter 136 may be incremented so as to write the time of day code from the block on the disc. In the event that recording is done successively on successive sectors of successive cylinders of the disc, the address of the sector of the disc which is being scanned, corresponds to the time of day and may be used as the time of day code without storing the code in a separate area of the disc. The sector addresses for writing and for reading are also inputted to the disc controller 134 from the processor. There are also cylinder addresses to identify the cylinder on which data is to be written or from which data is to be read. Separate data input and output lines for the second disc are also available to the disc controller 134. For further information respecting the disc controller and the disc reference may be had to the operating manual for the Diablo disc referred to above and to the Data General Interface Designers Manual also referred to above.

Figure 10D:
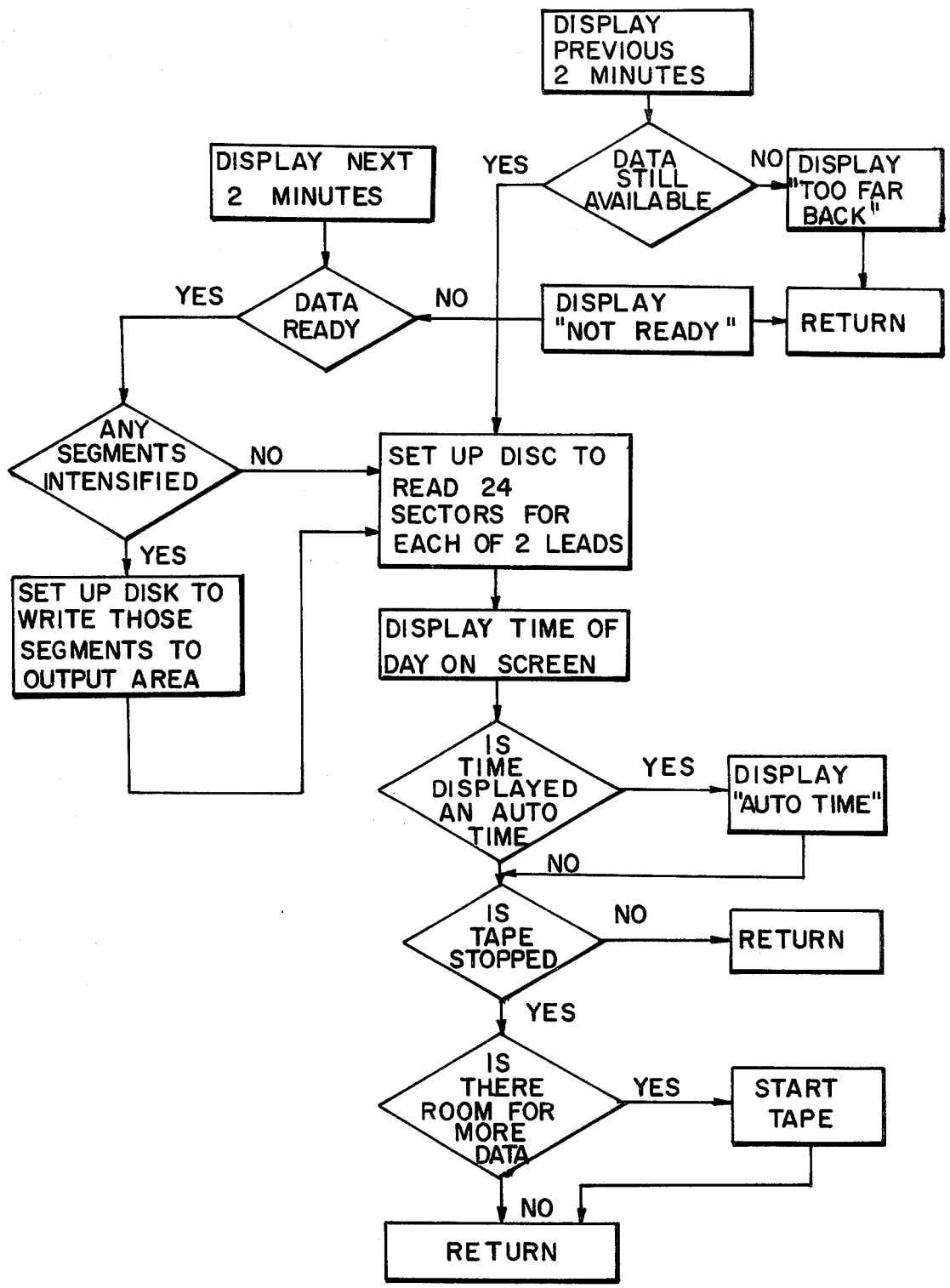

The operation of the display and analysis system as described in connection with the preceding figures will be more apparent from the flow charts of FIGS. 10A through 10E. The flow chart FIG. 10A shows the start section of the operation. The tape, which may be on a cassette, is first rewound at the outset of the start section. This is accomplished by pressing the key for rewind on the keyboard 20 (FIG. 1). Then the patient's number is entered via the keyboard. This number may be acknowledged by causing it to appear on the display screen. Then the start time (the time of day when the recording commenced) is entered. This time of day may also be acknowledged on the display. Then the auto times are requested by inputting the auto time times of day as auto time requests via the keyboard. When the time of day corresponding to an auto time occurs during the analysis of the tape, the display for that auto time has the words "auto time" written in the alphanumeric lines. The 2-minute display including an auto time will continually be displayed on the screen until the operator takes some action such as the intensification of a strip. The displays of the alphanumerics for acknowledgement purposes may be implemented through the processor 18 by blanking the ECG data section of the display.

It is desirable that the tape next be run in the forward direction to give the operator a quick over-view of several minutes of the tape thereby to enable verification of the integrity of the ECG signals. The tape is then rewound to the beginning.

Then the tape is started for analysis. ECG data is entered via the input control unit 16 as described in connection with FIG. 3. Interrupts are requested for each 30 seconds of data and the data in the blocks of 30 seconds each are transferred from the buffers in the memory of the processor 18 to the disc 26. The system then waits for an interrupt from the keyboard. Such interrupts may be commands to display the next two minutes of ECG data to intensify certain sections to display preceding sections of data. If no interrupts occur, the system waits for instructions from the operator. It is a feature of this system that the display is entirely under operator control. 2 minutes of data may be displayed for as long as the operator requires in order to accurately identify cardiac abnormalities which are to be noted in the report containing the strips of such data which is to be transmitted to the diagnosing physician.

When inputting new data from the tape into the system, the operations set forth in FIG. 10B are carried out. These operations constitute the sub-routine for writing the data onto the disc and is in the form of an interrupt service routine.

Referring to FIG. 10B, when tape data is ready, that is when a thirty second group of blocks is in the memory of the processor 18, the address of the blocks may be obtained from the time of day counter 136. This may be a counter in the processor which counts the data ready signals from the timing signal generator 38 (FIG. 3). The disc is then set up by being addressed to write six sectors for each of the two leads on each of the two discs 130 and 132. Then, if there is more room for data on the disc, the system will return to wait for the next address for the next six sectors of 30 seconds of ECG data which is to be written. If the disc is full, that is if there is eleven hours of data on the disc which has not been displayed, the address for the eleventh hour is recognized and used to automatically stop the tape. This sets a pointer register in the registers of the processor equal to 1, and also sets the general purpose register 76 (FIG. 6). The system then returns to a mode where it waits for interrupts such as an interrupt corresponding to a command to display the next 2 minutes of ECG data. When less than 2 hours of ECG data remains in storage and has not been examined, the tape is restarted. For a 24-hour tape, only one stop is normally required.

The interrupt service routine for intensification of a strip is shown in FIG. 10C. The intensify keys on the keyboard 20 generate an interrupt which is operated by the processor to convert a number (decimal 0 to 11) to a bit of a 12 bit word which is all zeros but for the one bit which corresponds to the strip to be intensified. In order to cancel or deintensify that word, the 12-bit word is exclusive ORed with the intensify word which is in the 12-bit register 114 (FIG. 6). The exclusively ORed word is then outputted to the intensify register. After intensification of the selected strip occurs, the system returns so that the intensification of another strip or other operation may be carried out.

FIG. 10D illustrates the operations performed when the 2-minute display is selected. The keyboard key for the next 2 minute display is actuated. If there is data on the disc the display will be produced. However, if there is no data ready this condition is recognized and the display will read "not ready" in the alphanumeric lines. The system then returns to wait for another request to display the next two minutes. By such time enough data will have been stored on the disc to enable a display to be formed. The sections which were intensified on the preceding 2-minute display are then transferred to the disc to write those sections in the 1000 strip output area. If no sections have been intensified on the preceding display, or after the intensified strip has been transferred to the output area, the disc is set up by being addressed to read 24 sectors or 2 minutes for each of the two leads out of each of the two disc units 130 and 132 (FIG. 7)

into the memory of the processor 18. The data is read out from the memory onto the display and the display is continuously refreshed until the next 2 minutes are selected. The time of day is displayed on the alphanumeric lines of the screen. If the time of day corresponds to an auto time the words "auto time" are displayed on the alphanumeric lines.

The display continues until some operator action occurs. If there is no auto time or after action has been taken with respect to the auto time, the function register (such as the general purpose register 76, (FIG. 6), is read to identify a tape stop condition. If the tape is not stopped the system returns to wait for an interrupt such as a keyboard request to display the next two minutes. If the tape is stopped, the system waits until there is room for at least 2 more hours of ECG data before starting the tape again. After the tape is started, the system returns to wait for another interrupt such as a request to display the next 2 minutes.

The system may work in reverse to display previous 2 minutes portions of the ECG signals. If several previous 2 minutes have been displayed, such that the data is beyond that which was recorded 1 hour previously to the first command for display of the previous 2 minutes, alphanumerics are written on the screen stating that the display is "too far back". The system then returns for another interrupt which should be a request to display the next 2 minutes of data. This next 2 minutes will be displayed as discussed above.

Figure 10E:
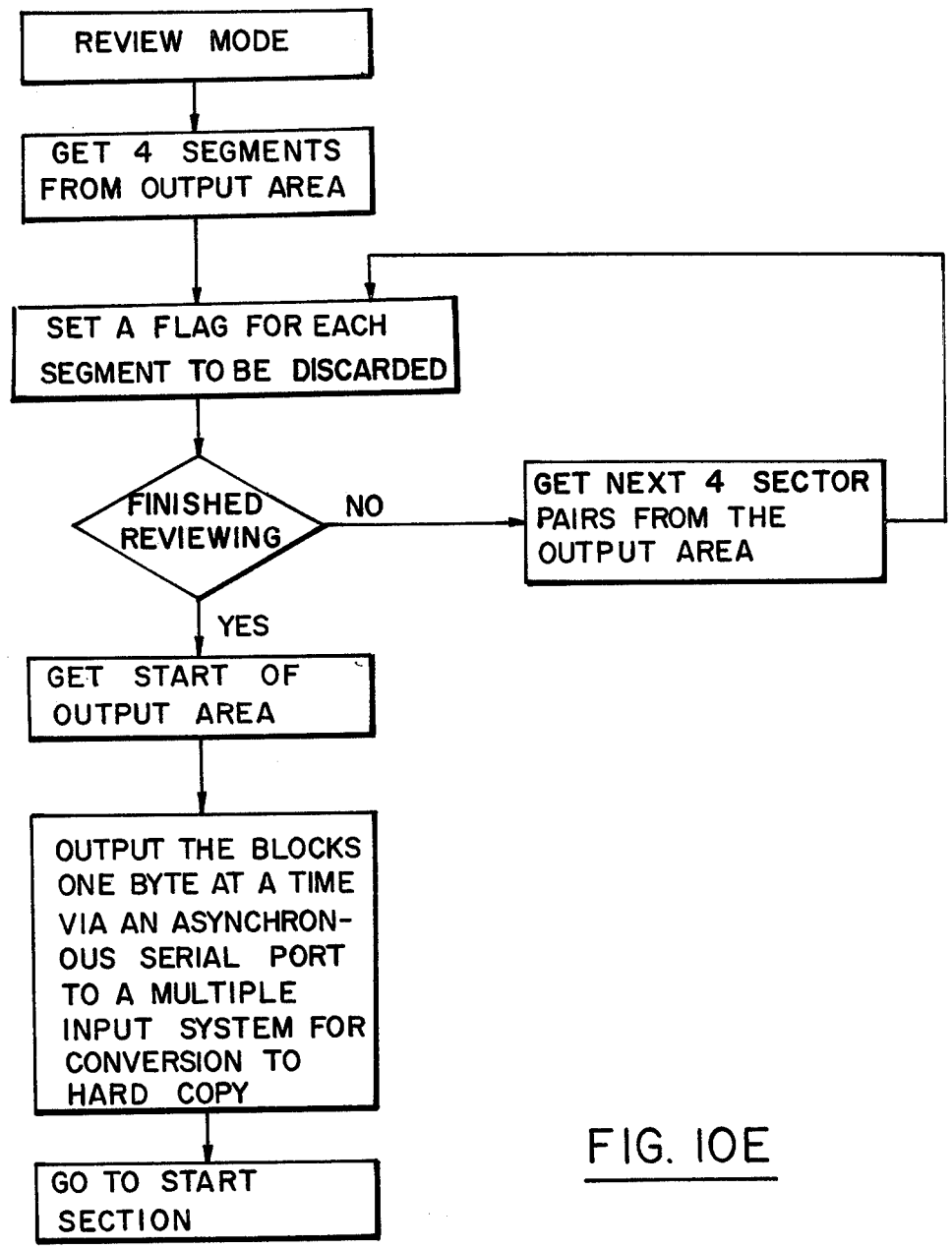

After the tape has been analyzed, the review mode is selected. The operations for carrying out the review mode are shown in FIG. 10E. Selection of the review mode is from the keyboard. The system then gets four sector pairs from the output area of the disc and stores them in the memory of the processor 18. One sector pair contains 1024 bytes which contain both alphanumeric and ECG data. The four sector pairs each contain 7½ seconds of ECG data and 250 bytes of alphanumeric data specifying the time of the strip and its lead type.

The display in the review mode consists of four ECG strips side by side below which there are four alphanumerics indicating the time of day of the corresponding strips. These are in one-to-one relationship so that the operator may recognize the time of day for the strips. As the operator reviews the strips, he sets a flag for each segment or strip to be discarded through the use of the keyboard. These flags are stored in the processor memory. After four strips are reviewed the operator selects the next four sector pairs and a corresponding alphanumeric data for review.

After all of the selected strips are reviewed the system is returned to the start of the output area; that is the selected sections and alphanumeric data corresponding thereto are again read out of the disc, one block at a time into the processors memory and then sent to the TTY output interface as described above. The port is connected to the plotter either directly or by way of a data link. The plotter converts the data into hard copy which is recorded to the diagnosing physician. After a report is completed the system is ready to go back to the start section (FIG. 10A) and another tape may be analyzed by repeating the same procedure. It will be appreciated of course that the program for carrying out these operations as shown in the flow charts of FIGS. 10A to 10E are stored as a program in the processor memory.

From the foregoing description it will be apparent that there has been provided an improved system for the display and analysis of the physiological signals particularly ECG signals which may be recorded over a long term and played back at much higher speeds. Variations and modifications in the hereindescribed system will undoubtedly suggest themselves to those skilled in the art. Accordingly, the foregoing description should be taken merely as illustrative and not in any limiting sense.

What is claimed is:

1. A system displaying physiological signals, such as signals which are reproduced at greater than real time after being recorded in real time for the observation of portions of said signals representing certain cardiac events, said system comprising
   memory means for receiving and holding data representing said reproduced signals,
   display means operated by data in said memory means for displaying on a plurality of separate, vertically displaced lines a plurality of successively occurring portions of said physiological signals, each of which portions have been recorded over a certain period of time, for observation, and
   control means adapted to be operated after each said observation for transferring to said displaying means from said memory means, data representing the next plurality of successively occurring portions for display on said plurality of lines.

2. The invention as set forth in claim 1 wherein said memory means includes storage means for receiving and holding all of said data representing said reproduced signals and first memory means for temporarily receiving from said storage means data representing at least a certain number of said plurality of portions which constitute a certain number of said lines, and said display means including display access means for transferring data from said first memory means to said display means.

3. The invention as set forth in claim 2 wherein said first memory means comprises means for formatting said reproduced signals representing data into blocks containing data representing at least one of said portions and holding said blocks in an area thereof, and
   storage means having means for receiving said blocks from said area of said first memory means and holding said blocks in a portion thereof.

4. The invention as set forth in claim 3 wherein said formatting means comprises means for converting said physiological signals as they are reproduced into consecutive bytes of said data, and buffer register means having storage for two words, each containing a pair of said bytes which are the alternate ones of said consecutive bytes, and input access means for transferring said words from said buffer register means to said first memory means, said display access means being operative to transfer alternate ones of said words to said display means.

5. The invention as set forth in claim 3 wherein said physiological signals are recorded continuously on tape, said system including transport means for continuously reproducing said tape, and control means for stopping reproduction of said tape transport means when a number of said words equal to the storage capacity of said storage means for said blocks is exceeded.

6. The invention as set forth in claim 3 further comprising means for deriving with said physiological signals, timing signals representing the relative time of day when said signals were recorded, means for formatting said timing signals into words corresponding to the time of day when each of said plurality of portions of said physiological signals were recorded and holding said time of day words in said first memory means, said storage means having portions thereof for receiving and holding said time of day words, and said display means including means for displaying numeric characters corresponding to said time of day words on lines adjacent to said lines of physiological signals.

7. The invention as set forth in claim 6 further comprising keyboard means for inputting words representing alphanumeric data correlated to said physiological signals to said first memory means for reception and holding therein, said storage means having portions for receiving and holding said alphanumeric words, and said means for displaying numeric characters also being operative to display said alphanumeric words on said adjacent lines.

8. The invention as set forth in claim 3 wherein said system includes processor means having a memory, and a magnetic disc bulk storage memory means, said processor memory providing said first memory means, and said magnetic disc providing said storage means.

9. The invention as set forth in claim 8 wherein said disc memory has a pair of discs, said physiological signals being reproduced separately in two different channels each for a separate simultaneous physiological signal recorded from a different lead, said first memory having separate ones of said areas dedicated to data representing the physiological signals from a different one of said channels, input access means for transferring said channels of said data to said separate first memory areas, and said storage means having means for transferring data from said separate first memory area to different ones of said discs.

10. The invention as set forth in claim 9 wherein said first memory means has other separate areas for temporarily receiving and holding blocks of data from different ones of said disc available for said display means, and said display means includes means for controlling said display access means for selectively displaying physiological signals corresponding to data held in said other separate areas.

11. The invention as set forth in claim 3 wherein said displaying means include oscilloscope means having X axis (horizontal) and Y axis (vertical deflection inputs and a Z (intensification) input, counter means for providing digital words corresponding to the vertical position of each of said lines along said Y axis to the displacement along the X axis of said lines, said display access means being responsive to said counter for fetching from said first memory means alternate ones of said words of said physiological signals data, digital to analog converter means for applying analog levels corresponding to bytes of said words and said counter words to the X and y inputs of said oscilloscope means to provide repeatedly traces of said physiological signals along successive ones of said lines so as to provide said display for observation.

12. the invention as set forth in claim 11 including converter means for storing a maxtrix of data representing a set of alphanumeric characters corresponding to data held in said first memory means, said display means including means for applying certain bits of said counter words to said digital to analog converter means for scanning a plurality of successive columns across at least one line adjacent to said lines along which said physiological signals are traced, means operated by said counter means for applying words of said data in said first memory means to said converter means to select different ones of said characters in said set, and means responsive to the bits of said words corresponding to successive position along each of said columns for applying data stored in said converter means to said Z input to produce data along said columns forming said alphanumeric characters.

13. A physiological signals display and analysis system for the observation and selection of certain portions of said signals which have characteristics representing certain physiological events, said system comprising
 means for displaying on a plurality of separate lines a plurality of successively occurring portions of said signals,
 memory means for containing data representing said signals, while said signals are being displayed,
 selection means for identifying data in said memory means which represents at least a section of each of said lines while said lines are being displayed,
 storage means for receiving and holding the data identified by said selection means, said identified data being received when the next plurality of successively occurring portions is displayed on said displaying means; and
 readout means utilizing the data held in said storage means to reproduce the signals in each of the identified sections of said lines.

14. The invention as set forth in claim 13 wherein said physiological signals are recorded over a long term consisting of a plurality of hours at a real time rate and said system includes means for reproducing said signals at a rate much greater than said real time rate, and data converter means for converting said signals into consecutive bytes of data for use in said memory means.

15. The invention as set forth in claim 14 including buffer register means for receiving and holding a plurality of pairs of said bytes in words consisting of a pair of said bytes, and input control means for locating different ones of said consecutive bytes in different ones of said words, such that the bytes in each word are spaced from each other by a like number of consecutive bytes.

16. The invention as set forth in claim 15 wherein said buffer register has storage for two said words and said control means is operative to locate those of said bytes which follow each other in odd numbered sequence in the first of said two words and those of said bytes which follow each other in even numbered sequence in the record of said two words.

17. The invention as set forth in claim 16, including means for transferring said words consecutively from said buffer register means to said storage means so as to constitute blocks of said consecutive words, each block consisting of data corresponding to a period of said physiological signals at least equal the duration of one of said portions thereof, display control means for transferring a plurality of said blocks which contain data representing said plurality of said signal portions to said memory means, and said display control means including display memory access means for transferring alternate words in said plurality of blocks consecutively to said displaying means to form said lines of said signal portions.

18. The invention as set forth in claim 17 wherein said memory means has certain first areas for receiving and holding data from said storage means and certain other areas for receiving and holding data from said buffer register means, said transferring means being operative to transfer said words from said buffer register means to said first areas of said memory means to form said blocks and said blocks from said first area to said storage means.

19. The invention as set forth in claim 18 wherein the record of said signals includes a timing signal synchronous with said recorded physiological signals, said timing signal containing information as to the time of day of occurrence of the physiological signals which are recorded concurrently therewith. Said transferring means being responsive to said timing signals for transferring said words from said buffer register to said memory means in synchronism therewith, and timing data input means responsive to the transfer of said blocks to said storage means for generating data representing the time of day of recording of the physiological signals represented by said blocks, and said displaying means including means for displaying the characters of said time of day data on a line adjacent to said lines of physiological signals.

20. The invention as set forth in claim 19 including keyboard means for inputting readable data representing the identity of said recorded physiological signals in alphanumeric format, said transferring means being operative to transfer said readable data to said storage means, and said display memory access means being operative to transfer said keyboard data means to said memory means after each of said blocks of physiological signals and time of day data for display on said lines adjacent to said physiological signal lines.

21. The invention as set forth in claim 18 wherein said display control means includes counter means for consecutively generating words representing the vertical locatin (Y) of each of said lines and the displacement (X) of each of said lines, said displaying means including an oscilloscope, and means responsive to said counter means words for generating traces to form said lines, and said display memory access means being responsive to said address words for transferring the bytes of said words in said memory means to said trace forming means so as to form said physiological signals along said lines.

22. The invention as set forth in claim 21, wherein said selection means includes register means for generating words corresponding to the counter means words for sections of said lines, means responsive to said register means and said counter means words for intensifying the traces along the sections of said lines corresponding thereto so as to identify said sections for observation, and means responsive to said register means word for transferring from said memory means to said storage means the words corresponding to said intensified sections.

23. The invention as set forth in claim 22 wherein said display control means includes means for changing the sequence in which said words in said memory means are transferred to said display means so as to shift the location of said physiological signals on said lines so as to locate said traces in sections of said lines identified by said selection means and enable transfer thereof to said storage means.

24. The invention as set forth in claim 22 wherein said readout means is a plotter for recording said selected sections of said line to provide hard copy thereof.

25. The invention as set forth in claim 22 including computer means having control, processing and memory units, said memory unit providing said memory means.

26. The invention as set forth in claim 25 wherein said storage means is a bulk storage memory unit separate from said computer means.

27. The invention as set forth in claim 26 wherein said bulk storage memory unit uses at least one magnetic disc record.

* * * * *